United States Patent [19]
Karasev et al.

[11] Patent Number: 5,257,623
[45] Date of Patent: Nov. 2, 1993

[54] APPARATUS FOR GENERATING ELECTRIC PULSES FOR BIOLOGICAL OBJECT STIMULATION

[76] Inventors: Alexandr A. Karasev, Mariupolskoe shosse, 27/1, kv. 164; Vladislav G. Zakharevich, ulitsa P. Tolyatti, 22/3, kv. 37; Alexandr N. Revenko, Mariupolskoe shosse, 27/1, kv. 90; Alexandr A. Kibirov, ulitsa Vodoprovodnaya, 19, kv. 47; Alexandr I. Dygai, ulitsa B. Bulvarnaya, 10,1, kv. 18, all of Taganrog; Alexandr I. Nechushkin, ulitsa B. Cherkizovskaya, 6, korpus 6, kv. 57, Moscow, all of U.S.S.R.

[21] Appl. No.: 635,552
[22] PCT Filed: Apr. 28, 1989
[86] PCT No.: PCT/SU89/00113
§ 371 Date: Dec. 31, 1990
§ 102(e) Date: Dec. 31, 1990
[87] PCT Pub. No.: WO90/10472
PCT Pub. Date: Sep. 20, 1990

[30] Foreign Application Priority Data

Mar. 6, 1989 [SU] U.S.S.R. ............... 4654349

[51] Int. Cl.$^5$ .............................................. A61N 1/36
[52] U.S. Cl. .................................................... 607/27
[58] Field of Search ........ 128/421, 422, 423, 419 PG, 128/419 D

[56] References Cited

U.S. PATENT DOCUMENTS

| | | |
|---|---|---|
| 2,713,120 | 7/1955 | Mostofsky et al. ................. 128/423 |
| 4,303,075 | 12/1981 | Heilman et al. .............. 128/419 PG |
| 4,505,275 | 3/1985 | Chen . |
| 4,669,477 | 6/1987 | Ober . |
| 4,733,667 | 3/1988 | Olive . |

FOREIGN PATENT DOCUMENTS

| | | |
|---|---|---|
| 0154976 | 9/1985 | European Pat. Off. . |
| 0196393 | of 1986 | European Pat. Off. . |
| 0145176 | 6/1988 | European Pat. Off. . |
| 865300 | 9/1981 | U.S.S.R. . |
| 921581 | 4/1982 | U.S.S.R. . |
| 1011130 | 4/1983 | U.S.S.R. . |
| 1022715 | 6/1983 | U.S.S.R. . |
| 1060192 | 12/1983 | U.S.S.R. . |
| 1069832 | 1/1984 | U.S.S.R. . |
| 1169669 | 7/1985 | U.S.S.R. . |
| 1222282 | 4/1986 | U.S.S.R. . |
| 1242185 | 7/1986 | U.S.S.R. . |
| 1378849 | 3/1988 | U.S.S.R. . |

Primary Examiner—Kyle L. Howell
Assistant Examiner—Kennedy J. Schaetzle
Attorney, Agent, or Firm—Lilling & Lilling

[57] ABSTRACT

The method comprises generating pulses of a specified repetition rate, duration modulating each pulse, composing packets of stimulating pulses with a specified packet duration and specified pause duration between pulse packets, and modifying the duration of the pulse packet applied to the object in accordance with an assessment of the electrophysiologic parameters of the state of the biological object's interelectrode section, this assessment being performed simultaneously with object stimulation. The apparatus comprises a pulse generator, a pulse duration modulator, a stimulating pulse power amplifier, a first signal shaper generating a signal indicative of the object's response to stimulating pulses, a variable-duration pulse generator providing pulse packet duration signals, a second signal shaper providing signals of pulse packet duration, and a modulation control signal clipper.

20 Claims, 10 Drawing Sheets

APPARATUS FOR GENERATING ELECTRIC PULSES FOR BIOLOGICAL OBJECT STIMULATION

FIELD OF THE INVENTION

The invention relates to electrotherapeutic apparatuses and, more specifically, to methods for generating electric pulses intended to stimulate biological objects and apparatuses thereof.

The invention can be used in clinical and sports medicine and as a personal instrument, in particular for the prophylaxis and treatment of diseases and pathologic states with affected compensatory and adaptation processes.

BACKGROUND OF THE INVENTION

Known in the art is a method for biological object stimulation, wherein electric pulses for stimulation are generated.

This method involves the following sequence of operations: stimulation by a standard stimulus is executed, followed by a test stimulation to detect the object's reaction, and then treatment stimulation by specially generated electric pulses of preset duration and repetition rate. These pulses are generated, amplified and used for stimulation during a certain time interval. After this, test stimulation is repeated to evaluate the effect of treatment stimulation and its results determine whether treatment should be continued or not (U.S. Pat. No. 4,505,275).

During the stimulation treatment interval the parameters of electric pulses generated according to this method remain unvariable and are not adaptable to the current state of the object. Multiple treatment stimulation prolongs the procedure, thus making overdosage more probable. All these factors lead to a reduced therapeutic effect.

Known in the art is a method for generating electric pulses for stimulating neural and muscular structures of the vehicular system and organs, residing in that pulses of a specified repetition rate are generated, each pulse is then duration-modulated and a pulse train of pulses of specified duration and duty factor is formed, with ramp (increase or decrease) variarion of the duration of pulses of a preset repetition rate. This pulse train is then amplified and applied to the biological object, setting an upper limit to the pulse duration in the train in accordance with the individual sensitivity of the biological object (SU, A, 1169669).

The parameters of the stimulating pulse trains are selected experimentally by the maximal object's response at physiologically comfortable conditions. Individual dosage is not provided, thus overdosage is possible. Pulses are not adapted to the current state of the object and all these factors reduce the overall therapeutic effect.

Known in the art is an apparatus for generating electric stimulating pulses, comprising a pulse generator, a modulator connected to the generator, an amplifier and an output stage (SU, A, 1069832).

The pulse voltage of rectangular waveform from the pulse generator is applied to an input of the modulator, the other input whereof receives pulses from a modulation frequency generator. At the modulator output, a pulse-modulated voltage with a carrier frequency of rectangular waveform is thus generated and passed to the amplifier, and thereafter to the biological object.

In this apparatus pulses of highly regulated, preset parameters are generated. It lacks the ability to assess the state of the biological object and dynamics of changes in this state, thus leading to unwarranted prolongation of the stimulation procedure and possible overdosage.

Also known in the art is an electrostimulator, comprising connected in series pulse generator, duration shaper, amplitude shaper in the form of a power amplifier, and an active electrode to be applied to a section of tissue (SU, A, 1011130).

Here the pulse generator produces pulses of the desired stimulation period, each pulse triggering the stimulus duration shaper, in turn controlling the amplitude shaper to generate current pulses passed via the electrodes.

This design configuration suffers the same deficiencies as the herein above discussed known in the art apparatus.

SUMMARY OF THE INVENTION

This invention is to provide a method for generating electric pulses for biological object stimulation and an apparatus thereof to generate electric pulses adaptable to the state of the biological object.

This is achieved by a method for generating electric pulses for biological object stimulation, comprising generation of pulses of a specified repetition rate, duration modulation of each pulse, generation of pulse packets of specified duration of packets and pauses between them and with ramp variation of the duration of pulses of the specified repetition rate, amplification of stimulation pulses constituting the pulse packet and applying these pulses to the biological object via the electrodes, and at the same time setting the maximal duration of pulses of the specified repetition rate in the pulse packets in accordance with the individual sensitivity of the biological object to stimulation treatment. According to the invention, the duration of the packet of stimulating pulses applied to the biological object is varied in accordance to evaluated electrophysiological parameters of the state of the interelectrode section of the biological object, this evaluation being carried out simultaneously with biological object stimulation.

It is expedient to use the impedance of the interelectrode section of the biological object as the electrophysiologic parameter, by which the state of the biological object is evaluated, using the time characteristics of the electric signal appearing after the trailing edge of each stimulating pulse to evaluate this impedance.

It is also possible to use the modified duration of the packet of stimulating pulses with a specified repetition rate, and, if the modified packet duration is less than a preset value, allowing the next packet of stimulating pulses to be passed to this given section of the biological object, or inhibiting further stimulation if the modified duration exceeds or is equal to a preset limiting value.

It is also expedient to generate complementary inverted electric pulses to affect the section of the biological object.

These and other objectives are achieved by an apparatus for generating electric pulses (electric pulse generator) for biological object stimulation, according to this invention, having a pulse generator, a pulse duration modulator with one input thereof connected to the pulse generator output, and a stimulating pulse power amplifier with the input thereof connected to the pulse duration modulator output and with the outputs thereof connected to the electrodes applied to a section of the biological object during stimulation. A first signal shaper has an input thereof connected to the output of the stimulating pulse power amplifier and has signals evaluating the biological object's response to stimulating pulse generated at the output thereof to control the duration of the stimulated pulses packet. A variable-duration pulse packet generator has an input thereof connected to the first signal shaper output. A second signal shaper generates a signal proportional to the stimulating pulse package duration and with leading and trailing edges varying at a constant rate and with the input thereof connected to the output of the variable-duration pulse generator. A modulation control signal clipper has one input thereof connected to a signal level presetter and has another input thereof connected to the second signal shaper output, with the modulation control signal clipper output connected to the second input of the pulse duration modulator.

The electric pulse generator may further comprise a time discriminator to generate a stimulation completion signal at its output, with one input of the time discriminator connected to the output of a time discriminator controller, the input whereof is connected to the output of the stimulating pulse power amplifier, and with the other input of the time discriminator connected to the variable-duration pulse generator output.

The second input of the time discriminator controller or the third input of the time discriminator may be connected to the pulse generator output.

It is advantageous that the electric pulse generator comprise a timer with the input thereof connected to the output of the time discriminator controller, and a controllable power supply with the input thereof connected to the timer output to disable the power supply, wherein the second input of the timer is connected to the pulse generator output.

It is also advantageous to connect the output of the time discriminator to the third input of modulation control signal clipper or the second input of the controllable power supply.

Furthermore, it proved to be advantageous that the electric pulse generator be complemented with a switch located between the electrodes and the stimulating pulse power amplifier.

The first signal shaper and the variable-duration pulse generator may be embodied as a multivibrator, designed with IGFETs, with resistors in the sources of transistors of the first stage and with a capacitor connected to the source of the p-channel transistor, so that the other capacitor lead constitutes the input to the first signal shaper. The first stage of the multivibrator is provided with a feedback loop of series connected diode and capacitor, wherein the output of the second stage of the multivibrator constitutes the output of the variable-duration pulse generator. The second signal shaper may be embodied as an IGFET integrator, with resistors between the voltage supply circuits and the transistor sources.

It is also advantageous that the pulse duration modulator comprise an IGFET amplifier with a differentiating network at the amplifier input, the time constant of this network variable by a separate IGFET, the gate whereof is connected to an input of the modulator and with the differentiating network input constituting the other input of the modulator.

The signal level presetter may comprise an IGFET integrator with resistors installed between the supply buses and the transistor sources and with the integrator input connected via switches to the voltage supply buses.

It proved suitable to embody the pulse generator with an IGFET multivibrator, with the first stage thereof comprising an IGFET amplifier, with an inertial resistor-capacitor network in the feedback loop, and with complementary IGFETs between the voltage supply buses and the transistor sources, the interconnected gates of these complementary IGFETs constituting the input of the first stage and the amplifier output constituting the output of the first stage of the multivibrator.

It is also advantageous that the time discriminator controller comprise series connected resistor and inverter, a first pulse counter with the data input thereof connected to the inverter output, the counter control input connected to its output and with the counter reset input constituting the controller input, a second pulse counter with the data input and thereof connected to the reset input of the first counter, with the control input of the second counter connected to its output and with the reset input of the second counter connected to the output of the first counter.

It is desirable that the time discriminator comprise an OR gate and a pulse counter with the reset input thereof connected to the OR gate output, the data input constituting the time discriminator input and the control input of the counter connected to its output.

It is also desirable that the controllable power supply comprise a voltage supply and a flip-flop with the set input thereof connected via a switch to the output of the voltage supply, with the reset inputs thereof constituting the inputs of the controllable power supply, and with the output thereof connected to the control input of an electronic key, the input whereof is connected to the voltage supply.

BRIEF DESCRIPTION OF THE DRAWINGS

The invention will now be described in greater detail with reference to specific embodiments thereof and to accompanying drawings, wherein:

FIG. 1 (a, b, c, d, e) shows the time diagrams of electric pulses across the electrodes;

BEST MODE FOR CARRYING OUT THE INVENTION

The method for generating electric pulses for biological object stimulation involves the following.

A sequence of rectangular pulses with a specified repetition rate is generated, these pulses are then duration modulated and arranged into packets of specified duration and specified pauses between packets. The duration of pulses of the specified repetition rate within a packet increases linearly to a maximal value, set in accordance with the individual sensitivity of the biological object, at which the patient experiences electric pricks of a subjectively comfortable character, then reducer linearly to zero.

Figure 1A:
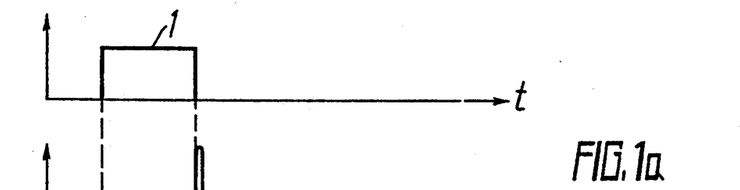
Figure 1B:
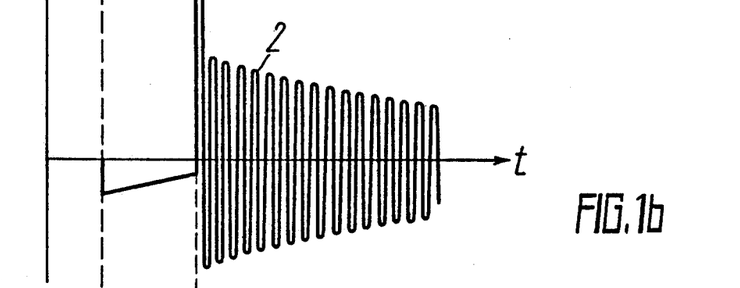

These packets of stimulating pulses 1 (FIG. 1a) are then amplified; an individual stimulating pulse 2 in the absence of contact with the biological object is shown in FIG. 1b.

Figure 1C:
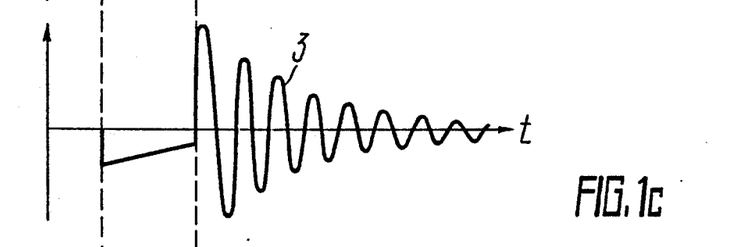
Figure 1D:
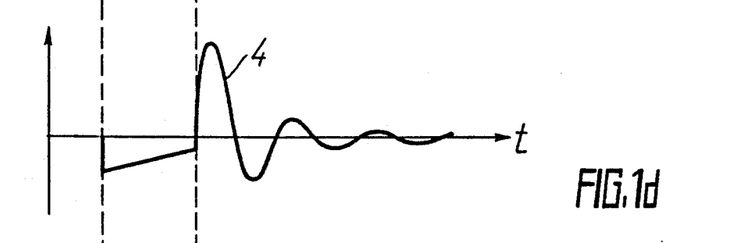
Figure 1E:
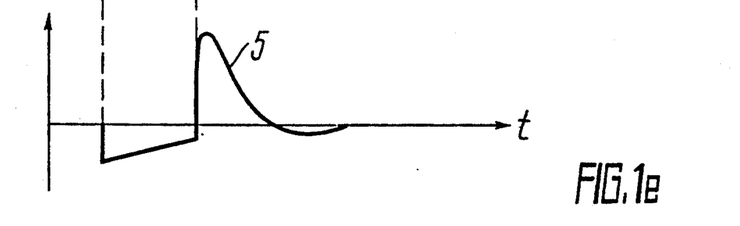

Amplified stimulating pulses 1 in packets are applied to the biological object and, depending on the state of the electrophysiologic parameters of the interelectrode section of the object, the stimulating pulses acquire the waveforms shown in FIG. 1c,d,e, depicting stimulating pulse waveforms at slight, medium and pronounced deviations of the electrophysiologic parameters from normal.

The interelectrode impedance of the section of the biological object is used as the electrophysiologic parameter, by which the state of the biological object is assessed.

The impedance is evaluated by the time characteristics 3, 4, 5 (FIG. 1c,d,e) of the electric signal appearing after each stimulating pulse 1 and the duration of the stimulating pulse packet is then varied accordingly and compared to a standard value.

If the pulse packet duration thus modified is less then the standard, the next packets of stimulating pulses are passed to the patient; if the modified duration exceeds the standard value, further application of stimulating pulse packets is discontinued.

To enhance the therapeutic effect, the herein above described sequence of operations is repeated with inverted stimulating pulses.

The dynamics of changes in the disorder caused by packets of stimulating pulses are used to select the site of subsequent stimulation, thus allowing the external energy application to be reduced and the procedure to be shortened, resulting in gradual contraction of the application area.

The electric pulse generator, implementing the herein above described method, according to the invention, comprises a pulse generator 6 (FIG. 2) with output 7 thereof driving input 8 of pulse duration modulator 9, stimulating pulse power amplifier 10 with input 11 thereof connected to output 12 of pulse duration modulator 9 and with output 13, 14 thereof connected to electrodes 15, 16, respectively, applied to section 17 of the biological object during stimulation.

Figure 2:
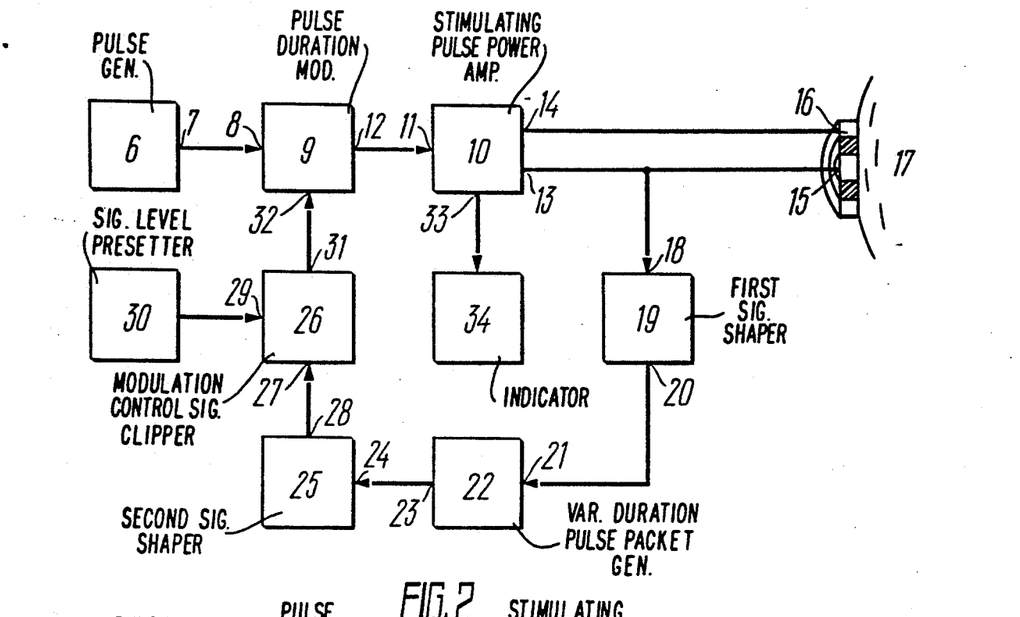
FIG. 2 shows the block diagram of the electric pulse generator, according to the invention.

The output of the amplifier 10 drives input 18 of signal shaper 19, wherein the response of the biological object to stimulation is determined and at the output 20 whereof a signal is generated to control the duration of the pulse packet. Output 20 of signal shaper 19 is passed to input 21 of variable-duration pulse packet generator 22, output 23 whereof is connected to input 24 of signal shaper 25, wherein a pulse corresponding to the duration of the pulse packet is generated with a leading and trailing edge of constant rate of change.

The electric pulse generator further comprises modulation control signal clipper 26 with input 27 thereof connected to output 28 of signal shaper 25 and with input 29 thereof connected to a signal level presetter 30, and with output 31 thereof driving second input 32 of pulse duration modulator 9. Output 33 of the power amplifier 10 is connected to an indicator 34.

Figure 3:
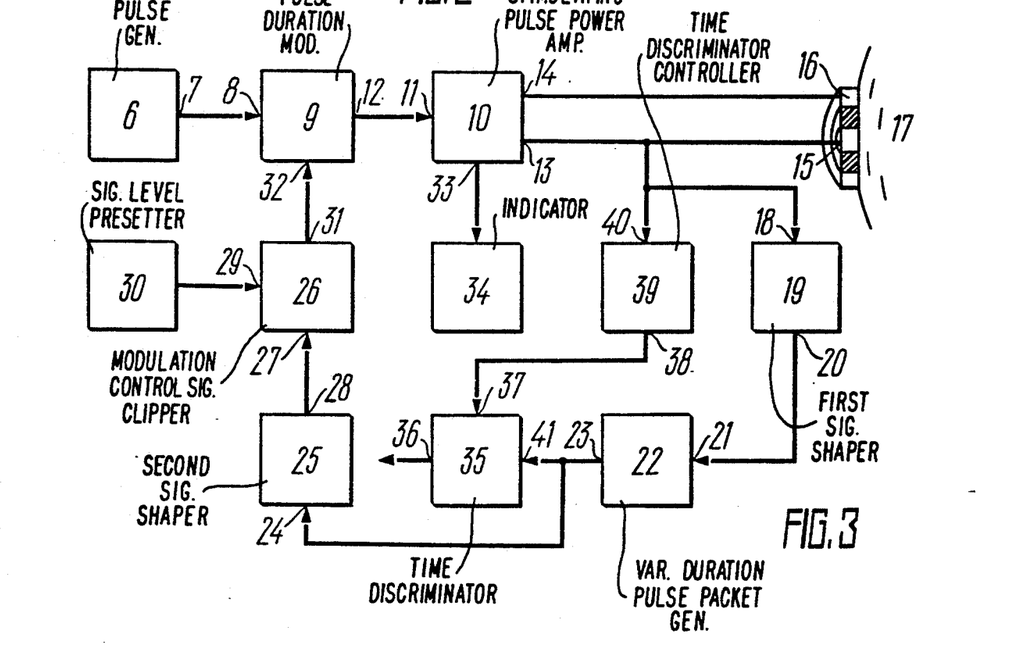
FIG. 3 shows the block diagram of the electric pulse generator with a time discriminator, according to the invention.

The electric pulse generator also comprises time discriminator 35 (FIG. 3), generating at output 36 thereof a stimulation discontinuation (limitation) signal and with input 37 thereof connected from output 38 of a time discriminator controller 39. Input 40 of the time discriminator controller 39 is connected to output 13 of the power amplifier 10 and input 41 of the time discriminator 35 is driven from output 23 of the variable-duration pulse generator 22.

Figure 4:
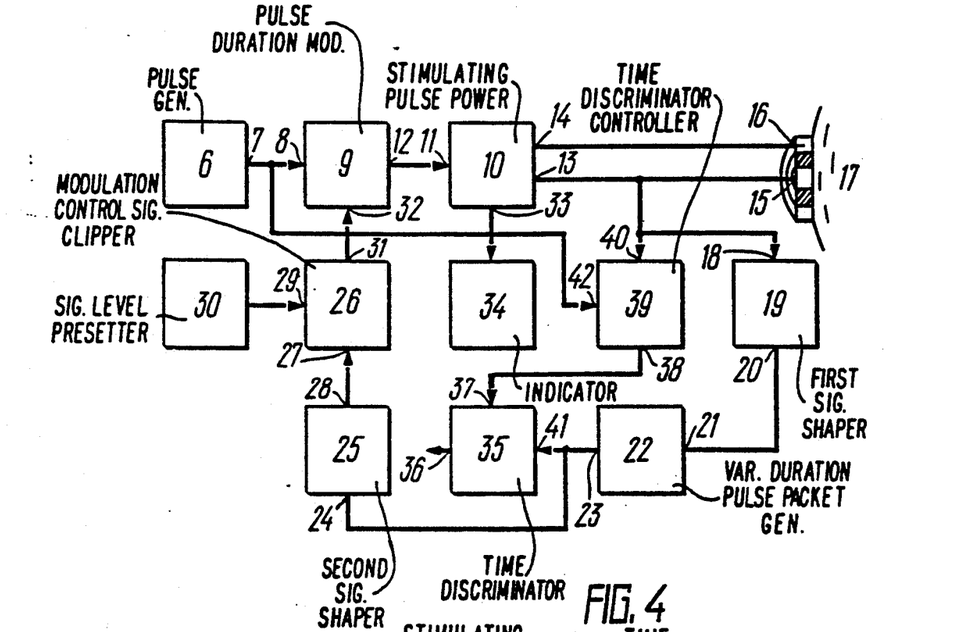
FIG. 4 shows another embodiment of the electric pulse generator shown in FIG. 3.
Figure 5:
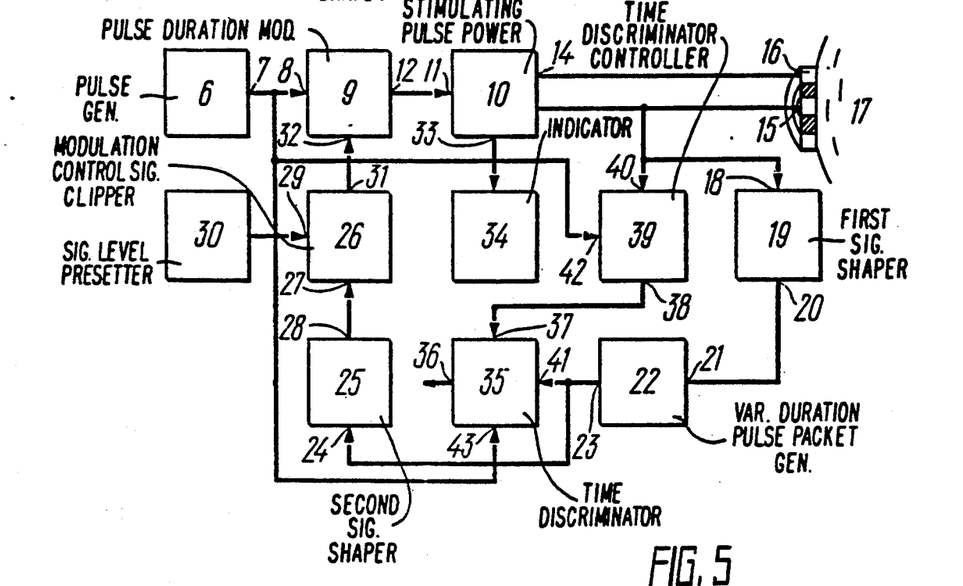
FIG. 5 shows yet another embodiment of the electric pulse generator, according to the invention.

The input 42 of the time discriminator controller 39 (FIG. 4) and input 43 of the time discriminator 35 (FIG. 5) are connected to output 7 (FIGS. 4, 5) of the pulse generator 6.

Figure 6:
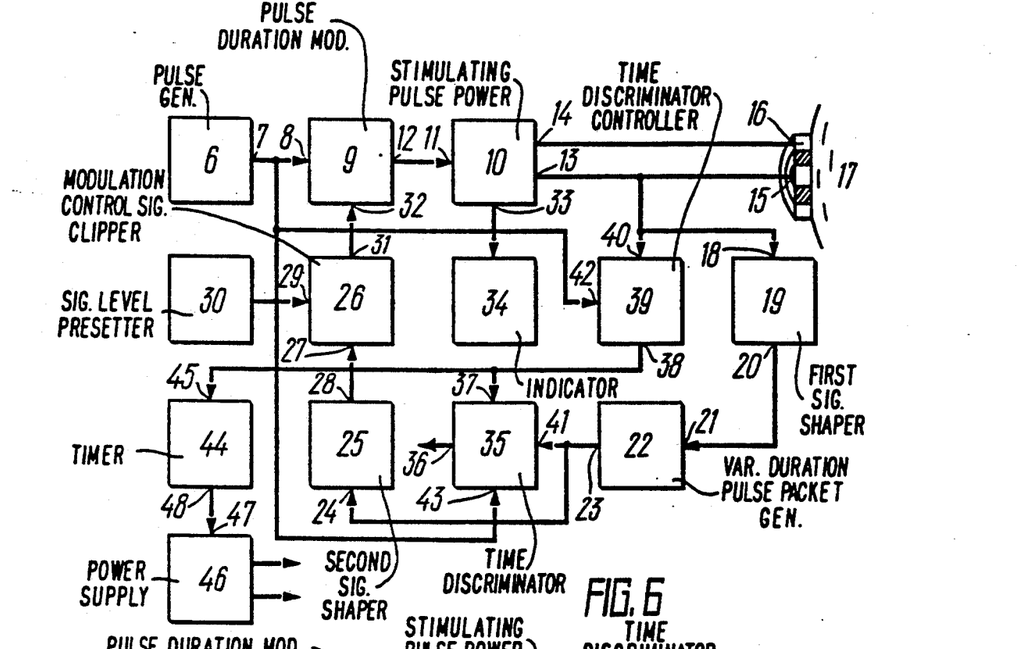
FIG. 6 shows the block diagram of an electric pulse generator with a timer, according to the invention.

The electric pulse generator also comprises timer 44 (FIG. 6), input 45 whereof is connected to output 38 of time discriminator controller 39, and controllable power supply 46 with input 47 thereof connected to output 48 of timer 44. An input 49 (FIG. 7) of the timer 44 is connected to output 7 of pulse generator 6.

Figure 8:
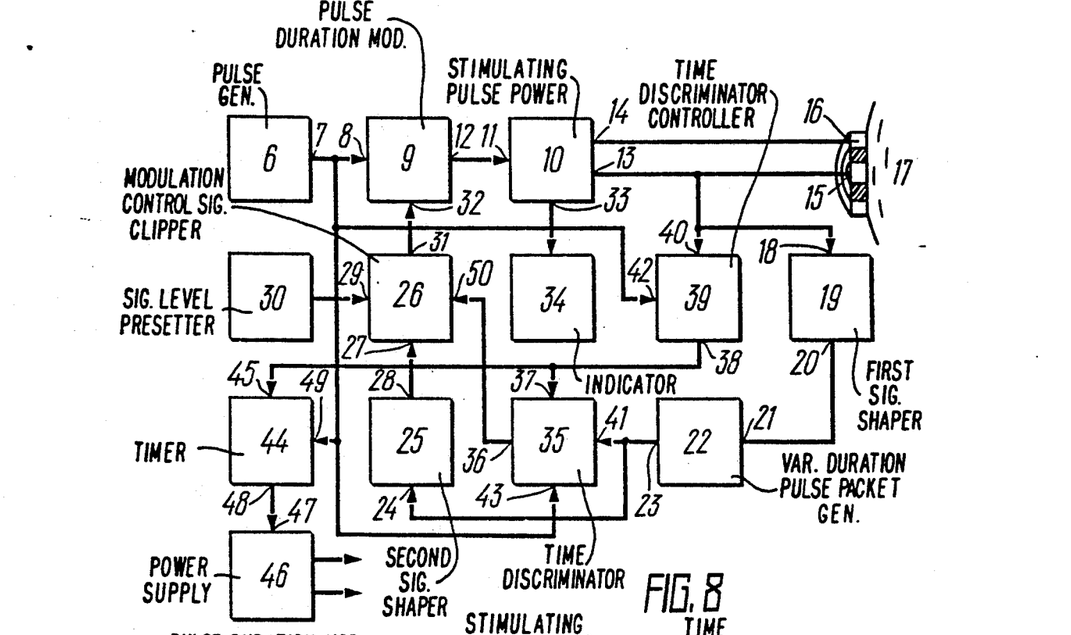
FIG. 8 shows the block diagram of the electric pulse generator with an embodiment of the stimulation energy limiting, according to the invention.

Output 36 (FIG. 8) of time discriminator 35 is connected to input 50 of modulator control signal clipper 26.

Figure 9:
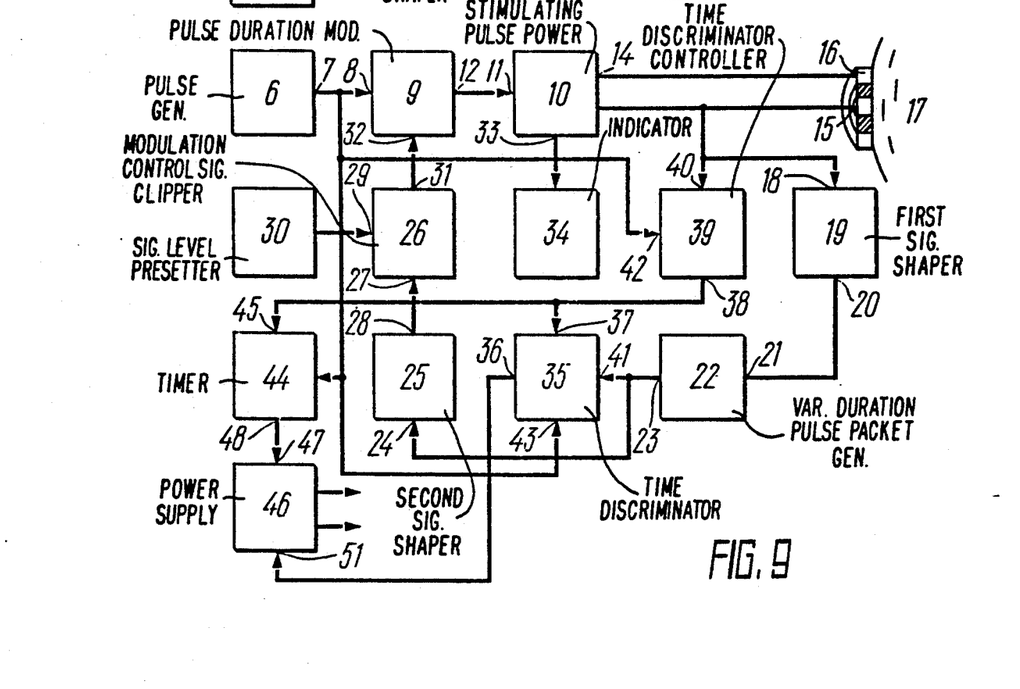
FIG. 9 shows the electric pulse generator shown in FIG. 8 with stimulation disabling, according to the invention.

In another embodiment (FIG. 9), output 36 of the time discriminator 35 is connected to input 51 of power supply 46.

In both embodiments, the electric pulse generator comprises electrode switch 52 (FIG. 10) inserted between outputs 13, 14 of power amplifier 10 and electrodes 15, 16 and having two states, thus allowing any electrode 15 (16) to be connected to each output 13 (14).

Figure 11:
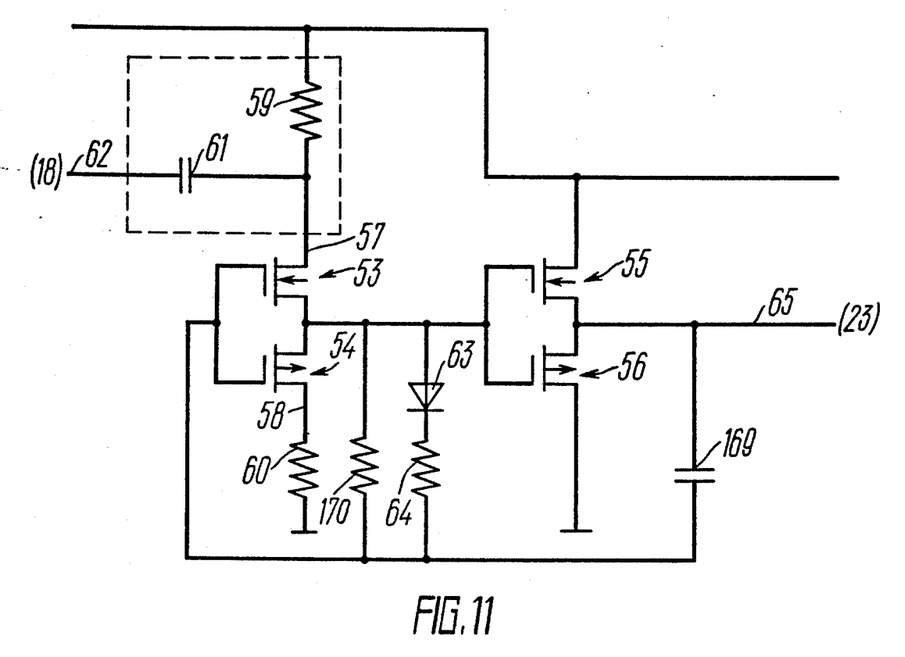
FIG. 11 is an electric schematic, showing the first signal shaper, according to the invention.

In the electric pulse generator, the first signal shaper 19 and variable-duration pulse generator 22 are embodied as an IGFET multivibrator with transistors 53 (FIG. 11), 54 and 55, 56, with resistors 59, 60 in the source 57, 58 circuits of transistors 53, 54 of the first stage and with capacitor 61 connected to source 57 of transistor 53, the other lead of capacitor 61 constituting input 18 (FIG. 2) of first signal shaper 19. The first stage is provided with a feedback loop of connected in series diode 63 (FIG. 11) and resistor 64 and output 65 of the multivibrator's second stage constitutes output 23 (FIG. 2) of variable-duration pulse generator 22.

Figure 12:
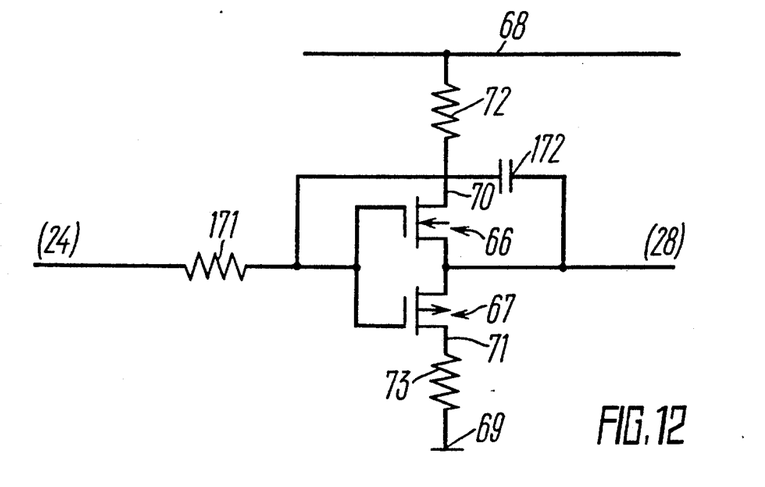
FIG. 12 is an electric schematic, showing the second signal shaper, according to the invention.

Second signal shaper 25 is embodied by an IGFET integrator with transistors 66 (FIG. 12) and 67 with resistors 72 and 73 inserted between supply buses 68, 69 and their sources 70, 71, respectively.

Figures 13, 14, 15:
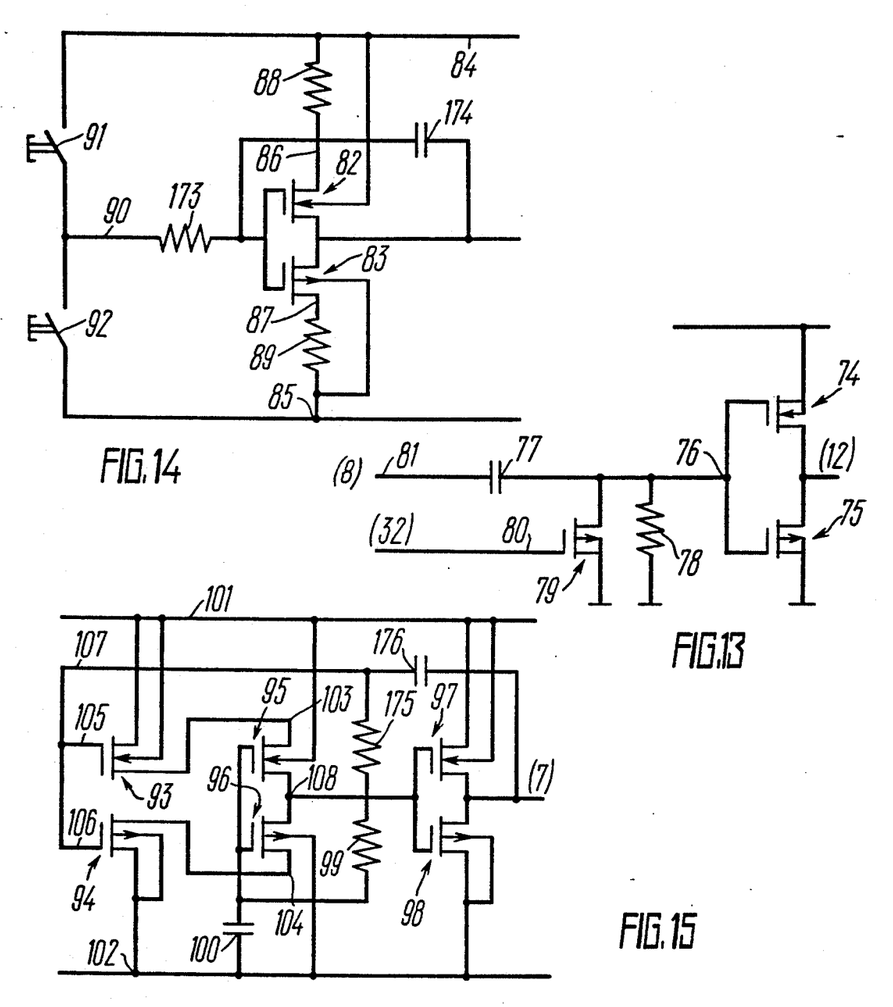
FIG. 13 is an electric schematic, showing the pulse duration modulator, according to the invention.
FIG. 14 is an electric schematic, showing the signal level presetter, according to the invention.
FIG. 15 is an electric schematic, showing the pulse generator, according to the invention.

Pulse duration modulator 9 (FIG. 2) comprises an IGFET amplifier designed with transistors 74 (FIG. 13) and 75, with a differentiating network at input 76 comprising capacitor 77 and restrictor 78 and featuring a time constance variable by controlling a separate IGFET 79, gate 80 whereof constitutes input 32 (FIG. 2) of pulse duration modulator 9, wherein input 81 (FIG. 13) of the differentiating network constitutes input 8 (FIG. 2) of pulse duration modulator 9.

Signal level presetter 30 comprises IGFET integrator embodied with transistors 82 (FIG. 14) and 83, with resistors 88, 89 installed between sources 86, 87 thereof and supply buses 84, 85, respectively, and with input 90 of the integrator connected to supply buses 84, 85 via switches 91, 92, respectively.

Pulse generator 6 (FIG. 2) is embodied by an IGFET multivibrator with transistors 93 (FIG. 15), 94, 95, 96, 97, 98, with the first stage thereof comprising an amplifier designed with transistors 95, 96, with an inertial network of resistor 99 and capacitor 100 in the feedback loop and with complementary IGFETs 93, 94 installed between their sources 103, 104 and supply buses 101, 102, respectively. Interconnected gates 105, 106 of complementary IGFETs 93, 94 constitute input 107 of the first stage and output 108 of amplifier 95, 96 constitutes the output of the multivibrator's first stage.

Figure 16:
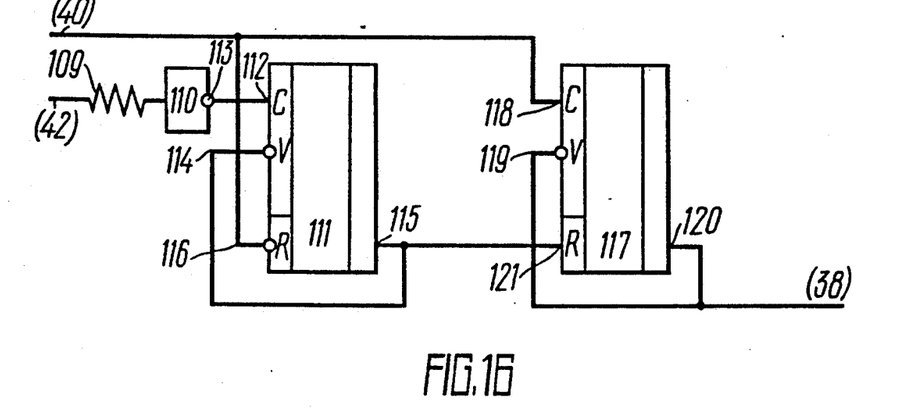
FIG. 16 is an electric schematic, showing the time discriminator controller, according to the invention.

Time discriminator controller 39 (FIG. 3) comprises series connected resistor 109 (FIG. 16) and inverter 110, and first pulse counter 111 with input 112 thereof connected to output 113 of the inverter 110 and with control input 114 thereof connected to output 115 of the counter 111.

Reset input 116 of pulse counter 111 constitutes input 40 (FIG. 3) of time discriminator controller 39. It further includes a second pulse counter 117 (FIG. 16) with the data input 118 thereof interconnected to reset input 116 of pulse counter 111. Control input 119 of pulse counter 117 is connected to its output 120 and reset input 121 is driven by pulse counter 111 output 115.

Figure 17:
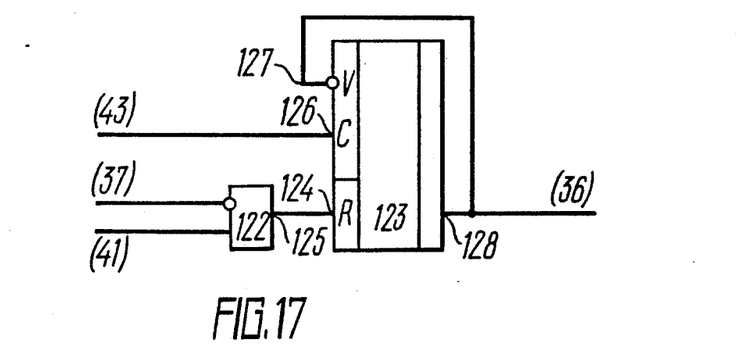
FIG. 17 is an electric schematic, showing the time discriminator, according to the invention.

Time discriminator 35 (FIG. 3) comprises OR gate 122 (FIG. 17) and pulse counter 123 with reset input 124 thereof connected to output 125 of OR gate 122. Data input 126 of pulse counter 123 constitutes input 43 (FIG. 3) of time discriminator 35 and control input 127 of pulse counter 123 (FIG. 17) is connected to its output 128.

Power supply 46 (FIG. 6) comprises voltage supply 129 (FIG. 18) and flip-flop 130, set input 131 whereof is connected to output 133 of voltage supply 129 via switch 132. Flip-flop 130 inputs 134 and 135 constitute inputs 47 and 51 (FIG. 6), respectively, of power supply 46 and output 136 (FIG. 18) of flip-flop 130 is connected to control input 137 of electronic key 138, input 139 whereof is connected to voltage supply 129.

Figure 18:
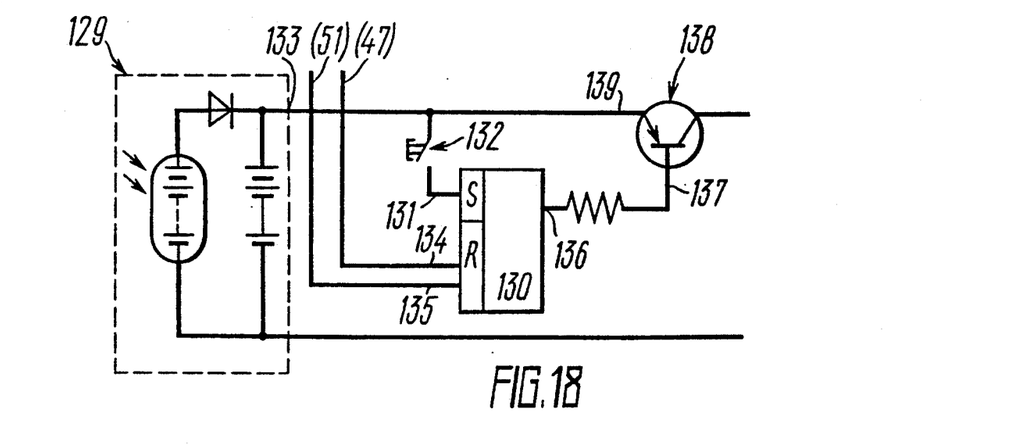
FIG. 18 is an electric schematic, showing the power supply according to the invention.

A set of galvanic cells and solar cells can serve as voltage supply 129, electronic key 130 may be designed with a transistor.

Figure 19:
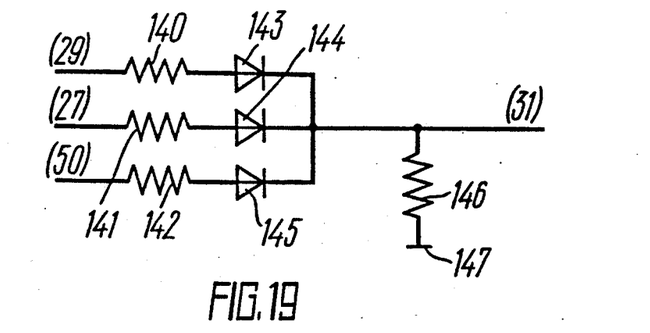
FIG. 19 is an electric schematic, showing the signal level clipper, according to the invention.

Modulation control signal clipper 26 (FIG. 2) comprises three networks of connected in series resistors 140 (FIG. 19), 141, 142 and diodes 143, 144, 145, respectively. The other leads of diodes 143, 144, 145 are interconnected into a common point and connected to output 31 (FIG. 2) of modulation control signal clipper 26 and, via resistor 146 (FIG. 19), to common bus 147.

Figure 20:
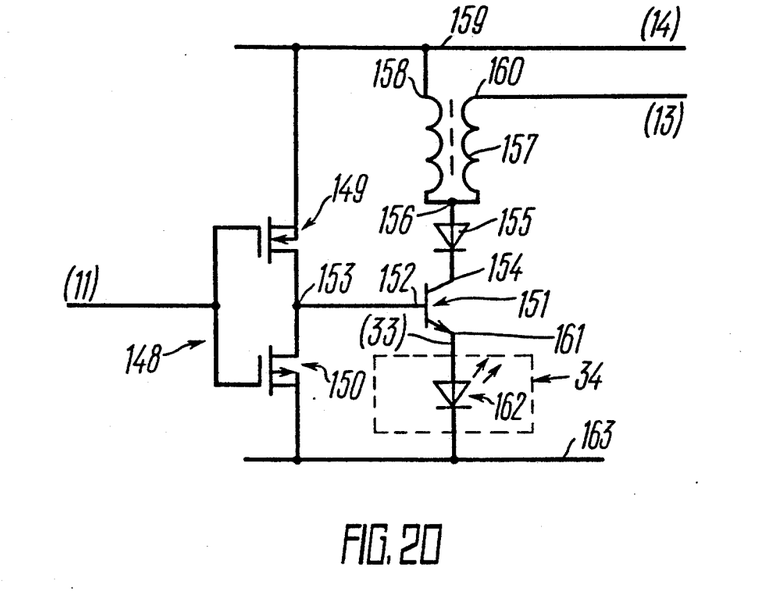
FIG. 20 is an electric schematic, showing the power amplifier, according to the invention

Power amplifier 10 (FIG. 2) and indicator 34 comprise amplifier 148 (FIG. 20) designed with IGFETs 149, 150 and transistor 151, base 152 whereof is connected to output 153 of amplifier 148 and collector 154 whereof is connected to tap 156 on inductance coil 157 via diode 155. The first of the lead Inductance coil 157 is connected to supply bus 159 and second lead 160 constitutes the first output 13 (FIG. 2) of power amplifier 10, second output 14 whereof is connected to supply bus 159 (FIG. 20). The emitter 161 of the transistor 151 is connected to third output 33 (FIG. 2) of power amplifier 10 and is connected to indicator 34, comprising diode 162 (FIG. 20) connected to common bus 163.

Figure 7:
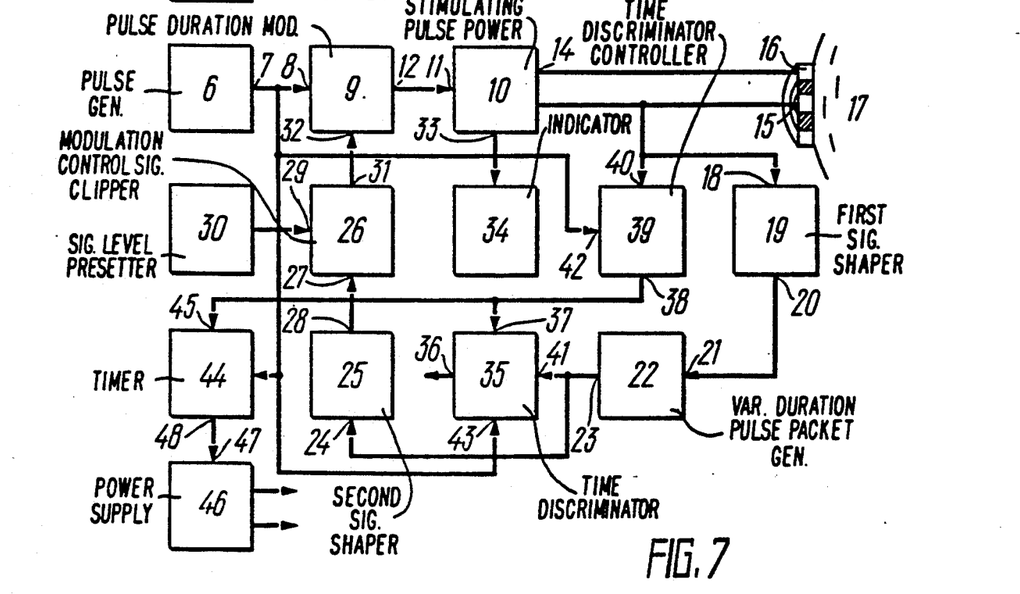
FIG. 7 shows another embodiment of the electric pulse generator with a timer, according to the invention.
Figure 21:
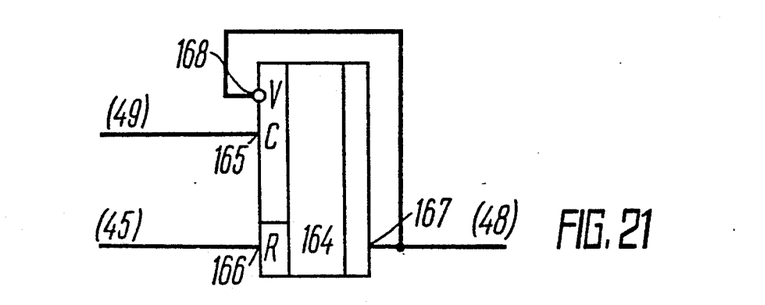
FIG. 21 is an electric schematic, showing the timer, according to the invention.

Timer 44 (FIG. 7) comprises pulse counter 164 (FIG. 21) with data input 165 thereof connected to input 49 of timer 44 (FIG. 7) and with reset input 166 thereof (FIG. 21) connected to input 45 of timer 44 (FIG. 7). Output 167 of pulse counter 164 (FIG. 21) is connected to its control input 168 and to output 48 (FIG. 7) of timer 44.

In the descriptions of embodiments of individual units of the electric pulse generator certain components were omitted. Thus, for instance, signal shaper 19 (FIG. 2) comprises time-setting capacitor 169 (FIG. 11) and resistor 170, signal shaper 25 (FIG. 2) comprises resistor 171 (FIG. 12) and capacitor 172, signal level presetter 30 (FIG. 2) has time-setting resistor 173 (FIG. 14) and capacitor 174, and pulse generator 6 (FIG. 2) has time-setting resistor 175 (FIG. 15) and capacitor 176.

Figure 10:
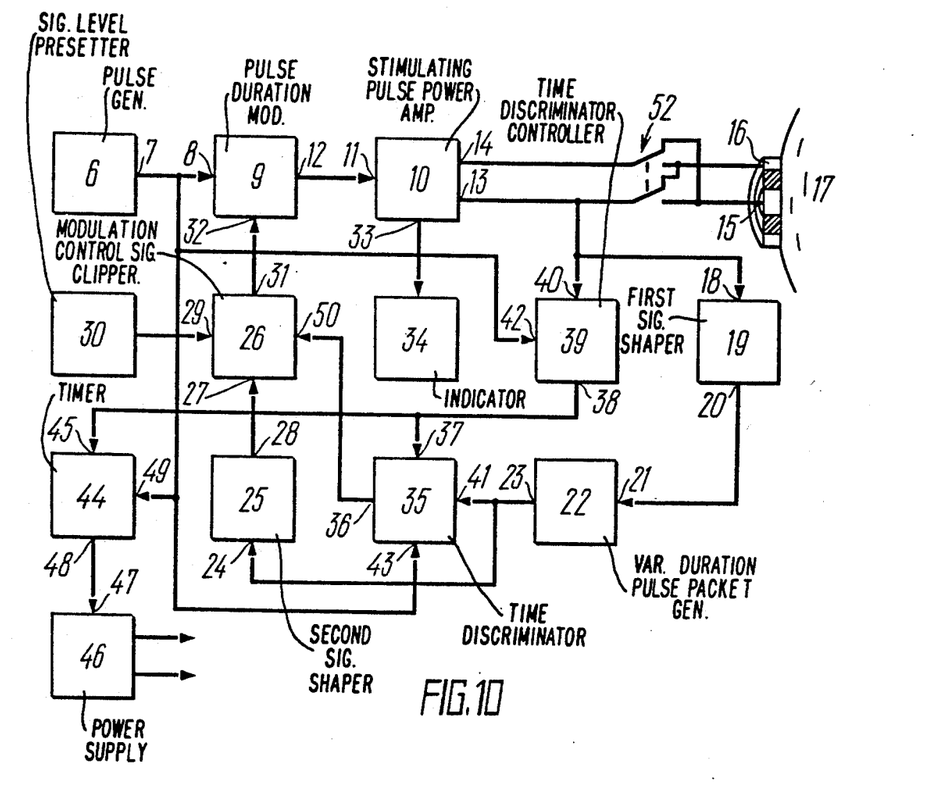
FIG. 10 shows the block diagram of the electric pulse generator with an electrode switch, according to the invention.

The electric pulse generator of the invention shown in FIG. 10 functions as follows.

The electric pulse generator is turned on by momentarily closing switch 132 in power supply 46, thereby causing the signal from output 136 of flip-flop 130 to enable electronic key 138 and thus pass the supply voltage to all units of the electric pulse generator.

Pulse generator 6 functions similarly to known in the art devices of similar purpose, but features a low power consumption. A sequence of rectangular pulses of a specified repetition rate is generated at output 7 of pulse generator 6 and then passed to input 8 of modulator 9.

Modulator 9 modulates the duration of pulses arriving at its input, shortening their duration in proportion to the signal level at its input 32, down to zero. Functioning of modulator 9 is similar to that of known in the art devices of similar purpose.

Duration modulated stimulating pulses from output 12 of modulator 9 are applied to input 11 of power amplifier 10.

Inductance coil 157 in power amplifier 10 functions as a step-up autotransformer to provide high-voltage pulses at output 13 of power amplifier 10, to be then applied to electrode 15. Electrode 16 is the neutral (indifferent) electrode and is connected via output 14 of power amplifier 10 to supply bus 159. The duration of pulses on electrode 15 is evaluated by the intensity of glow of indicator 34.

In its initial state, generator 22 generates pulses at output 23 of rectangular waveform, the duration whereof sets the duration of pulse packets. Generator 22 varies the duration of its output pulses in arrordance to the signal at its input 21, without affecting the duration of pauses between pulses.

Pulses from output 23 of generator 22 are passed to signal shaper 25, wherein pulses with linearly rising leading edges and linearly decaying trailing edges are generated at its output 28.

These pulses are applied to input 27 of clipper 26, wherein the pulse amplitude is limited to a value set by presetter 30 at the input 29 of clipper 26. A rise or decrease of the signal level generated by presetter 30 is produced by closing switch 92 or 91, respectively.

Thus, clipper 26 generates at its output 31 negative-going pulses with ramp leading and trailing edges and a duration corresponding to the pulse packet duration, with a preset duration of pauses between pulses and of a minimal value set by the signal level at input 29 of clipper 26.

The limited pulses are then passed to input 32 of modulator 9 to generate at its output 12 packets of rectangular stimulating pulses with linear increase of pulse duration within the packet to a value set by presetter 30, with a set duration of pauses between pulse packets.

In the absence of contact of electrodes 15, 16 and section 17 of the biological object, pulses 2 (FIG. 1b) at output 13 of power amplifier 10 feature a high frequency and relatively low damping, so that the signal at output 20 of shaper 19 is insufficient to change the operation mode of generator 22.

Time discriminator controller 39 discriminates the oscillation frequency of the signal at its input 40, functioning similarly to known in the art devices of similar purpose, but features a higher accuracy of frequency discrimination due to the use of digital techniques and due to synchronization by the pulse sequence arriving from output 7 of generator 6.

Thus, at a high oscillation frequency, e.g. of pulse 2 (FIG. 1b), at input 40 of controller 39, a signal inhibiting time discriminator 35 and enabling timer 44 is generated at output 38 of controller 39.

To improve the accuracy of time interval setting, timer 44 is embodied with digital techniques and is synchronized by the pulse sequence from output 7 of generator 6.

The presence of a high oscillation frequency at input 40 of controller 39 during the time interval set by timer 44, this corresponding to the absence of contact to section 17 of the biological object, causes timer 44 to generate at its output 48 a signal, passed to input 47 of power supply 46, to turn off the entire electric pulse generator.

Contact between electrodes 15, 16 and section 17 of the biological object causes the electrode signals to acquire characteristics depending on the state of the biological object, i.e. characteristics 3, 4, 5 (FIG. 1c, d, e) and the signal at output 20 of signal shaper 19 to become sufficient to control the duration of pulses generated by generator 22. Since the process at input 40 of controller 39 in this case features a relatively low frequency, a signal resetting and inhibiting timer 44 and simultaneously enabling time discriminator 35 is generated at output 38 of controller 39.

Time discriminator 35 compares the duration of pulses arriving from generator 22 to a standard value and functions similarly to the known in the art device of similar purpose, but is implemented using digital techniques to improve the accuracy of time interval generation and is synchronized by the pulse sequence from output 7 of pulse generator 6.

During stimulation the state of the biological object varies, thus causing changes in the process characteristics (FIG. 1) at output 13 of power amplifier 10, so that at a certain moment of time the signal at output 20 of signal shaper 19 sets the pulse duration of pulses from generator 22 equal to or greater than the standard value. This results in time discriminator 35 generating at its output 36 a signal to be applied via clipper 26 to control input 32 of modulator 9 to reduce the duration of stimulating pulses to a minimum value, consequently reducing the possibility of overdosage.

Steady-state operation conditions are maintained while electrodes 15, 16 are in contact with section 17 of the object, and initial conditions are automatically restored in the absence of such contact, as described herein above.

To enhance the therapeutic effect, switch 52 is provided between outputs 13, 14 of power amplifier 10 and electrodes 15, 16 to interchange the active and neutral electrodes.

The electric pulse generator of the invention, shown in FIGS. 9, 11-21, differs from that described herein above in that the signal from output 36 of time discriminator 35 is applied to input 51 of power supply 46 and turns off the electric pulse generator's power supply, thus excluding stimulation overdosage of a specific section 17 of the biological object.

Thus, disappearance of the contact between electrodes 15, 16 and the biological object does not reset the electric pulse generator and therefore there is not need for restarting.

Functioning of electric pulse generators illustrated in FIGS. 2 to 8 is similar to the herein above described because they represent but various embodiments.

The method and apparatus thereof of the invention, herein above described, have been tested in clinical hospitals, with the results presented herein below.

This methodology has been applied to a large group of patients with disorders of the peripheral neutral system with root and neurotic disfunctions, static and dynamic disorders, diseases of the ambulatory apparatus of diverse aetiology (inflammatory, metabolic, traumatic, genetic, etc.), with disorders of the central neural system accompanied by liquor/dynamic disfunctions, cerebral blood circulation disorders and their consequences, with inflammations of the respiratory tract, diseases of the alimentary tract, vegetative neural system and other pathologic states with disorders of adaptation processes.

Osteochondrosis of the neck and lumbar parts with vascular and root and statico-dynamic disorders were the most numerous amoung peripheral neural system diseases. Before treatment, the acute stage duration varied from 3 to 5 days to 2.5 to 3 months, ar various disease durations. The findings include: stimulation time is a strictly individual factor, shorter at shorter acute stages and good compensatory capabilities of the patient's organism and has to be lengthened in case of prolonged acute stages and long-term diseases.

The check group consisted of ten persons who received complex therapy, including acupuncture reflex therapy. Positive results after treatment include not only lessening of organic and functional focal point changes, but psycho-emotional changes as well. Stimulation was applied locally, segmentary, 3 to 15 procedures daily once in two days or twice a week. The patients treated included walk-in patients and patients hospitalized in the neurology department.

The method of this invention shortens the time of treatment of both walk-in and hospitalized patients, when used both as the only treatment and in combination with other methods of treatment. The treatment was noted to be easily endurable, no side effects were detected. Positive results have been obtained when treating other kinds of pathologic states.

In six cases the "placebo" effect was checked and electrostimulation was performed with the aid of other known similar equipment; in all cases the "placebo" effect was detected by the features and effect of stimulation.

The following clinical tests were carried out to justify the criteria of dosage adequacy for individual stimulation.

Twenty patients with peripheral neural system disorders, root manifestations, with similar statico-dynamic disorders, with up to three days of recurrent acute stage, and durations of disease up to five years, sanguinics and cholerics in neural type, 12 male and 8 female, were divided into three groups.

The first group consisted of five males and three females received treatment on sections of the skin above affected vertebrae and paravertibrary, with the tissue impedance being evaluated, till levelling-off of the results, with only polarity of the electrode signals (using the methodology of individually dosed stimulation).

The second group consisted of two males and four females and received a similar stimulation, but with changes of electrode signal polarity.

The third group, of five males and one female, after individually dosed stimulation received forced treatment (double exposure at a constant polarity).

Changes in the statico-dynamic disorder and root disorder states were checked with examinations prior to stimulation, after stimulation and after each treatment session.

Positive therapeutic effect was obtained in all groups, as evidenced by improved statico-dynamic indices of the verterbrae, reduced prolapsus of roots (this maintained after the procedure but again increased to the next session). The therapeutic effect was accompanied by changes in the emotional background and the general well-being of the patient. The greatest clinical effect was noted in patients of the second group, which required a smaller number of treatment sessions (3 to 4) to attain rehabilitation, as compared to 4 to 6 sessions for patients of the first group and 6 to 10 sessions for patients of the third group.

In the third group forced stimulation was found to reduce the clinical achievements of dised stimulation by 5 to 7%.

Dynamic examinations of all patients after 6 to 7 months did not reveal any relapses. Patients of the third group noted periodic unpleasant paraesthesia accompanied by limited vertebrae mobility.

The method of the invention allows its applications for electrostimulation with individual dosage, providing reduced external energy application, individual exposure, reduced duration of subsequent treatment session due to selection of the application site. The electric pulse generator of the invention implements the method of the invention automatically and therefore features a low power consumption. The action of the electric pulse generator affects the compensatory and adaptation processes in the organism.

The total time of treatment is reduced and hospitalization time is shortened by 5 to 10 days and more.

The electric pulse generator may be used by operators without special training and even by the patient himself, without additional instructions.

Use of the electric pulse generator allows combining treatment with monitoring of the patient's state.

INDUSTRIAL APPLICABILITY

The invention can be used in clinical and sports medicine, and as a personal instrument, in particular for prophylaxis and treatment of diseases and pathologic states, involving disorders of the compensatory and adaptation processes.

We claim:

1. An electric pulse generator providing pulses for stimulating biological objects, comprising a pulse generator means with an output for generating pulses; a pulse duration modulator means for modulating the duration of said pulses from said pulse generator and producing a stimulating pulse packet with a first input connected to the output of the pulse generator, a second input and an output; a stimulating pulse power amplifier means for amplifying the amplitude of pulses of said stimulating pulse packet and having a first input connected to the output of the pulse duration modulator means and having outputs; electrodes for application to a section of the biological object's tissue for stimulation thereof, and connected to first and second outputs of said stimulating pulse power amplifier means; a first signal shaper means for producing a control signal to control the duration of the stimulating pulse packet and said first signal shaper means having an input connected to the second output of the stimulating pulse power amplifier means and having an output at which said control signal is produced to control the duration of the stimulating pulse packet; a variable pulse packet duration generator means for providing signals to detect the response of the biological object to stimulating pulses and having an input connected to the output of said first signal shaper means and having an output; a second signal shaper means for producing signals with a duration equal to that of the stimulating pulse packet and with the amplitude of leading and trailing edges varying at a constant rate and having an input connected to the output of the variable pulse packet duration generator means, and an output; a modulation control signal clipper with a first input connected to the output of the second signal shaper means, a second input and an output connected to the second input of the pulse duration modulator means; and, a signal level presetter connected to said second input of said modulation control signal clipper.

2. A generator as claimed in claim 1, wherein said modulation control signal clipper further includes a third input; further comprising a time discriminator with an output connected to said third input of said modulation control signal clipper, with a first input connected to the output of said variable pulse packet duration generator, and with a second input; a time discriminator controller with inputs connected to the second output of said stimulating pulse power amplifier and the output of said pulse generator, and an output connected to said second input of said time discriminator.

3. A generator as claimed in claim 2 wherein said time discriminator comprises an OR gate and a pulse counter with a reset input connected to an output of said OR gate, with a data input constituting a third input of said time discriminator, and with a control input connected to an output of said pulse counter.

4. A generator as claimed in claim 2 wherein said time discriminator controller comprises series connected resistor and inverter, a first pulse counter with a data input connected to an output of inverter, with a control input connected to an output of said first pulse counter, and with a reset input constituting the input of said time discriminator controller, and a second pulse counter with a data input interconnected with the reset input of said first pulse counter, with a control input of said second pulse counter connected to an output of said second pulse counter, and with a reset input connected to the output of said first pulse counter.

5. A generator as claimed in claim 4, wherein said time discriminator comprises an OR gate and a pulse counter with a reset input connected to an output of said OR gate, with a data input constituting a third input of said time discriminator, and with a control input connected to an output of said pulse counter.

6. A generator as claimed in claim 5, wherein said controllable power supply comprises a voltage supply and a flip-flop with a set input connected via a switch to an output of said voltage supply, with reset inputs constituting the inputs of said controllable power supply, and with an output connected to a control input of an electronic key, an input of said electronic key being connected to said voltage supply.

7. A generator as claimed in claim 2 further comprising a timer with an input connected to the output of said time discriminator controller, and an output; a controllable power supply with an input connected to the output of said timer and wherein said timer generates a signal at said output of said timer to disconnect the power supply.

8. A generator as claimed in claim 7, wherein said controllable power supply comprises a voltage supply and a flip-flop with a set input connected via a switch to an output of said voltage supply, with reset inputs constituting the inputs of said controllable power supply, and with an output connected to a control input of an electronic key, an input of said electronic key being connected to said voltage supply.

9. A generator as claimed in claim 7, wherein a second input of said timer is connected to the output of said pulse generator.

10. A generator as claimed in claim 7, wherein the output of said time discriminator is connected to a second input of said controllable power supply.

11. A generator as claimed in claim 1 or 2 further comprising a switch connected between said electrodes and said stimulating pulse power amplifier.

12. A generator as claimed in claim 1 or 2, further comprising supply buses wherein said second signal shaper is an integrator with IGFET transistors, with resistors connected between said supply buses and sources of said transistors.

13. A generator as claimed in claim 1 or 2, wherein said pulse duration modulator comprises an amplifier designed with IGFETs, with a differentiation network at an input of said amplifier, a network time constant controlled by a separate FET, a gate of said FET being connected to the second input of said pulse duration modulator and with an input of the differentiating network constituting the first input of said pulse duration modulator.

14. A generator as claimed in claim 1 or 2, wherein said signal presetter comprises and integrator designed with IGFETs, with resistors connected between supply buses and the sources of said IGFETs and with an input of the integrator connected to supply buses via switches.

15. A generator as claimed in claims 1 or 2, wherein said pulse generator is designed as a multivibrator with IGFETs, a first stage of said multivibrator comprising an amplifier designed with IGFETs, provided with a feedback loop with an inertial link comprising a resistor and a capacitor, with supplementary FETs connected between supply buses and sources of said IGFETs of the first stage, and with gates of said supplementary FETs interconnected and constituting an input of the first stage and with an output of the amplifier constituting an output of the first stage of the multivibrator.

16. A generator as claimed in claims 1 or 2 wherein said first signal shaper and said variable duration pulse generator are designed as a multivibrator with IGFETs, with resistors in transistor source circuits of a first stage and with a source of a p-channel transistor connected to one lead of a capacitor, another lead of said capacitor serving as the input of said first signal shaper, wherein the first stage of the multivibrator is provided with a feedback loop of a series connected diode and resistor and the output of a second multivibrator stage constitutes the output of said variable-duration pulse generator.

17. A generator as claimed in claim 16, further comprising supply buses wherein said second signal shaper is an integrator with IGFET transistors, with resistors connected between supply buses and sources of said transistors.

18. A generator as claimed in claim 17, wherein said pulse duration modulator comprises an amplifier designed with IGFETs, with a differentiating network at an input of said amplifier, a network time constant controlled by a separate FET, a gate of said FET being connected to the second input of said pulse duration modulator and with an input of the differentiating network constituting the first input of said pulse duration modulator.

19. A generator as claimed in claim 18, wherein said signal presetter comprises an integrator designed with IGFETs, with resistors connected between supply buses and the sources of said IGFETs, and with an input of the integrator connected to supply buses via switches.

20. A generator is claimed in claim 19, wherein said pulse generator is designed as a multivibrator with, IGFETs, a first stage of said multivibrator comprising an amplifier designed with IGFETs, provided with a feedback loop with an inertial link comprising a resistor and a capacitor, with supplementary FETs connected between supply buses and, sources of said IGFETs of the first stage, and with gates of said supplementary FETs constitute interconnected and constituting an input of the first stage and with an output of the amplifier constituting an output of the first stage of the multivibrator.

* * * * *